United States Patent
Misra et al.

(10) Patent No.: US 10,286,116 B2
(45) Date of Patent: May 14, 2019

(54) METHODS AND MATERIALS FOR REDUCING VENOUS NEOINTIMAL HYPERPLASIA OF AN ARTERIOVENOUS FISTULA OR GRAFT

(71) Applicant: Mayo Foundation for Medical Education and Research, Rochester, MN (US)

(72) Inventors: Sanjay Misra, Rochester, MN (US); Allan B. Dietz, Chatfield, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/097,070

(22) Filed: Apr. 12, 2016

(65) Prior Publication Data

US 2016/0303170 A1    Oct. 20, 2016

Related U.S. Application Data

(60) Provisional application No. 62/166,241, filed on May 26, 2015, provisional application No. 62/147,762, filed on Apr. 15, 2015.

(51) Int. Cl.
| | | |
|---|---|---|
| A61K 35/12 | (2015.01) | |
| A61K 35/28 | (2015.01) | |
| A61L 27/36 | (2006.01) | |
| A61L 31/00 | (2006.01) | |
| A61L 27/38 | (2006.01) | |
| A61L 27/50 | (2006.01) | |

(52) U.S. Cl.
CPC ............ *A61L 31/005* (2013.01); *A61K 35/12* (2013.01); *A61K 35/28* (2013.01); *A61L 27/3633* (2013.01); *A61L 27/3834* (2013.01); *A61L 27/507* (2013.01)

(58) Field of Classification Search
None
See application file for complete search history.

(56) References Cited

U.S. PATENT DOCUMENTS

| | | | | |
|---|---|---|---|---|
| 5,620,687 A | * | 4/1997 | Hart | A61K 39/395 424/130.1 |
| 5,770,609 A | * | 6/1998 | Grainger | A61K 9/0024 514/319 |
| 5,773,479 A | * | 6/1998 | Grainger | A61K 31/00 514/651 |
| 7,070,616 B2 | * | 7/2006 | Majercak | A61F 2/2418 623/1.24 |

(Continued)

OTHER PUBLICATIONS

Abdel Aziz et al., "Therapeutic potential of bone marrow-derived mesenchymal stem cells on experimental liver fibrosis," *Clin Biochem.*, 40(12):893-899, Epub May 3, 2007.

(Continued)

*Primary Examiner* — Blaine Lankford
(74) *Attorney, Agent, or Firm* — Fish & Richardson P.C.

(57) ABSTRACT

This document provides methods and materials involved in reducing venous neointimal hyperplasia (VNH) of an arteriovenous fistula (AVF) or graft. For example, methods and materials for using stem cells (e.g., mesenchymal stem cells), extracellular matrix material, or a combination of stem cells and extracellular matrix material to reduce VNH of AVFs or grafts are provided.

4 Claims, 12 Drawing Sheets

Specification includes a Sequence Listing.

(56) References Cited

U.S. PATENT DOCUMENTS

| | | | | |
|---|---|---|---|---|
| 7,419,678 | B2* | 9/2008 | Falotico | A61F 2/91 424/423 |
| 7,775,965 | B2* | 8/2010 | McFetridge | A61L 27/3604 600/36 |
| 8,568,761 | B2* | 10/2013 | Matheny | A61K 38/39 424/423 |
| 9,198,668 | B2* | 12/2015 | Theobald | A61B 17/12172 |
| 9,333,068 | B2* | 5/2016 | El-Kurdi | A61F 2/06 |
| 2005/0096735 | A1* | 5/2005 | Hojeibane | A61F 2/2418 623/1.24 |
| 2008/0208323 | A1* | 8/2008 | El-Kurdi | A61F 2/06 623/1.36 |
| 2010/0204783 | A1 | 8/2010 | Nugent et al. | |
| 2011/0264190 | A1 | 10/2011 | McClain et al. | |
| 2011/0288036 | A1* | 11/2011 | Lander | A61K 38/16 514/21.4 |
| 2012/0283618 | A1 | 11/2012 | Livesey et al. | |
| 2013/0035712 | A1* | 2/2013 | Theobald | A61B 17/12172 606/198 |

OTHER PUBLICATIONS

Bansal et al., "Novel (89)Zr cell labeling approach for PET-based cell trafficking studies," *EJNMMI Res.*, 5:19, eCollection 2015, Mar. 28, 2015.
Caplan, "Why are MSCs therapeutic? New data: new insight," J Pathol., 217(2):318-324, Jan. 2009.
Collins et al., "US Renal Data System 2013 Annual Data Report," *Am J Kidney Dis.*, 63(1 Suppl):A7, Jan. 2014.
Crespo-Diaz et al., "Platelet lysate consisting of a natural repair proteome supports human mesenchymal stem cell proliferation and chromosomal stability," *Cell Transplant*, 20(6):797-811, Epub Nov. 19, 2010, Print 2011.
Das et al., "Hypoxia exposure induces the emergence of fibroblasts lacking replication repressor signals of PKCzeta in the pulmonary artery adventitia," *Cardiovasc Res.*, 78(3):440-8. Epub Jan. 24, 2008.
Das et al., "The role of hypoxia in bone marrow-derived mesenchymal stem cells: considerations for regenerative medicine approaches," *Tissue Eng Part B Rev.*, 16(2):159-168, Apr. 2010.
De Marchi et al., "Risk factors for vascular disease and arteriovenous fistula dysfunction in hemodialysis patients," *J Am Soc Nephrol.*, 7(8):1169-1177, Aug. 1996.
Dukkipati et al., "Association of vascular access type with inflammatory marker levels in maintenance hemodialysis patients," *Semin Dial.*, 27(4):415-423, Epub Oct. 9, 2013, print Jul.-Aug. 2014.
Faigel et al., "Endoscopic-guided portal injection chemotherapy for hepatic metastases," *Endosc Ultrasound.*, 3(Suppl 1): S1, Apr. 2014.
Faigel et al., "EUS-Guided Portal Injection of Chemotherapy (EPIC) for Hepatic Metastases," Poster Presentation; American Gastroenterological Association; Chicago, Illinois; May 2014, 1 page.
Faigel et al., "Mo1924 Feasibility of EUS-Guided Portal Injection of Chemotherapy (EPIC) Using Irinotecan-Loaded Microbeads for the Treatment of Hepatic Metastases," *Gastroenterol.*, 146(5):S692-S693, May 2014.
Faigel, "EUS-Guided Portal Injection Chemotherapy (EPIC) for Hepatic Metastases," Oral Presentation; 11th EUROEUS Congress; Paris, France; Apr. 2014, 16 pages.
Hartl et al., "A role for MCP-1/CCR2 in interstitial lung disease in children," *Respir Res.* 6:93, Aug. 11, 2005.
Hu et al. "Transplantation of hypoxia-preconditioned mesenchymal stem cells improves infarcted heart function via enhanced survival of implanted cells and angiogenesis," *J Thorac Cardiovasc Surg.*, 135(4):799-808, Apr. 2008.
Janardhanan et al. "Simvastatin reduces venous stenosis formation in a murine hemodialysis vascular access model," *Kidney Int.* 84(2):338-352, Epub May 1, 2013.
Juncos et al., "MCP-1 contributes to arteriovenous fistula failure," *J Am Soc Nephrol.*, 22(1):43-48, Epub Nov. 29, 2010, print Jan. 2011.
Kanno et al., "Angiotensin II participates in hepatic inflammation and fibrosis through MCP-1 expression," *Dig Dis Sci.*, 50(5):942-948, May 2005.
Lata et al., "The role of short-term oxygen administration in the prevention of intimal hyperplasia," *J Vasc Surg.*, 58(2):452-459, Epub Feb. 1, 2013.
Lee et al., "Association of artery wall hypoxia and cellular proliferation at a vascular anastomosis," *J Surg Res.*, 91(1):32-37, Jun. 1, 2000.
Li et al., "Cellular and morphological changes during neointimal hyperplasia development in a porcine arteriovenous graft model," *Nephrol Dial Transplant.*, 22(11):3139-46. Epub Jun. 30, 2007.
Li et al., "Paracrine action mediate the antifibrotic effect of transplanted mesenchymal stem cells in a rat model of global heart failure," *Mol Biol Rep.*, 36(4):725-731, Epub Mar. 27, 2008, print Apr. 2009.
Liao et al., "Enhanced MCP-1 release by keloid CD14+ cells augments fibroblast proliferation: role of MCP-1 and Akt pathway in keloids," *Exp Dermatol.*, 19(8):e142-e150, Aug. 2010.
Liu et al., "Effect of bone marrow mesenchymal stem cells transplantation on expression of NFB and PCNA and vascular stenosis after carotid artery balloon injury of rabbit," *Heart*, 96(Suppl 3):A24, Abstract e0073, Oct. 1, 2010.
Liu et al., "Microinflammation is involved in the dysfunction of arteriovenous fistula in patients with maintenance hemodialysis," *Chin Med J (Engl).*, 121(21):2157-2161, Nov. 5, 2008.
Mattana et al., "Leukocyte-polytetrafluoroethylene interaction enhances proliferation of vascular smooth muscle cells via tumor necrosis factor-alpha secretion," *Kidney Int.* 52(6):1478-1485, Dec. 1997.
Misra et al., "Adventitial remodeling with increased matrix metalloproteinase-2 activity in a porcine arteriovenous polytetrafluoroethylene grafts," *Kidney Int.*, 68(6):2890-2900, Dec. 2005.
Misra et al., "Expression of hypoxia inducible factor-1 alpha, macrophage migration inhibition factor, matrix metalloproteinase-2 and -9, and their inhibitors in hemodialysis grafts and arteriovenous fistulas," *J Vasc Interv Radiol.*, 19(2 Pt 1):252-259, Feb. 2008.
Misra et al., "Increased expression of HIF-1alpha, VEGF-A and its receptors, MMP-2, TIMP-1, and ADAMTS-1 at the venous stenosis of arteriovenous fistula in a mouse model with renal insufficiency," *J Vasc Interv Radiol.*, 21(8):1255-1261, Epub Jul. 3, 2010.
Nagaya et al., "Transplantation of mesenchymal stem cells improves cardiac function in a rat model of dilated cardiomyopathy," *Circulation* 112(8):1128-1135, Epub Aug. 15, 2005.
Ninichuk et al., "Multipotent mesenchymal stem cells reduce interstitial fibrosis but do not delay progression of chronic kidney disease in collagen4A3-deficient mice," *Kidney Int.*, 70(1):121-129, Epub May 24, 2006.
Ohnishi et al., "Mesenchymal stem cells attenuate cardiac fibroblast proliferation and collagen synthesis through paracrine actions," *FEBS Lett.* 581(21):3961-3966, Epub Jul. 23, 2007.
Okuma et al., "C-C chemokine receptor 2 (CCR2) deficiency improves bleomycin-induced pulmonary fibrosis by attenuation of both macrophage infiltration and production of macrophage-derived matrix metalloproteinases," *J Pathol.*, 204(5):594-604, Dec. 2004.
Ortiz et al., "Mesenchymal stem cell engraftment in lung is enhanced in response to bleomycin exposure and ameliorates its fibrotic effects," *Proc Natl Acad Sci U S A.* 100(14):8407-11. Epub Jun. 18, 2003.
Oyagi et al., "Therapeutic effect of transplanting HGF-treated bone marrow mesenchymal cells into CCl4-injured rats," *J Hepatol.*, 44(4):742-748, Epub Dec. 9, 2005.
Papayianni et al., "Circulating levels of ICAM-1, VCAM-1, and MCP-1 are increased in haemodialysis patients: association with inflammation, dyslipidaemia, and vascular events," *Nerohrol Dial Transplant.*, 17(3):435-441, Mar. 2002.
Pittenger et al., "Multilineage potential of adult human mesenchymal stem cells," *Science*, 284(5411):143-147, Apr. 2, 1999.
Potapova et al., "Mesenchymal stem cells support migration, extracellular matrix invasion, proliferation, and survival of endothelial cells in vitro," *Stem Cells*, 25(7):1761-8. Epub Mar. 29, 2007.

(56) References Cited

OTHER PUBLICATIONS

Prockop et al., "Clinical trials with adult stem/progenitor cells for tissue repair: let's not overlook some essential precautions," *Blood*, 109(8):3147-3151, Epub Dec. 14, 2006, print Apr. 15, 2007.
Ramasamy et al., "Mesenchymal stem cells inhibit dendritic cell differentiation and function by preventing entry into the cell cycle," *Transplantation*, 83(1):71-76, Jan. 15, 2007.
Ramasamy et al., "Mesenchymal stem cells inhibit proliferation and apoptosis of tumor cells: impact on in vivo tumor growth," *Leukemia*, 21(2):304-310, Epub Dec. 14, 2006, print Feb. 2007.
Rekhter et al., "Cell proliferation in human arteriovenous fistulas used for hemodialysis," *Arterioscler Thromb.*, 13(4):609-617, Apr. 1993.
Riella et al., "Vascular access in haemodialysis: strengthening the Achilles' heel," *Nat Rev Nephrol.*, 9(6):348-357, Epub Apr. 16, 2013.
Rotmans et al., "Hemodialysis access graft failure: time to revisit an unmet clinical need?" *J Nephrol.*, 18(1):9-20, Jan.-Feb. 2005.
Roy-Chaudhury et al., "Hemodialysis vascular access dysfunction: from pathophysiology to novel therapies," *Blood Purif.*, 21(1):99-110, 2003.
Roy-Chaudhury et al., "Venous neointimal hyperplasia in polytetrafluoroethylene dialysis grafts," *Kidney Int.*, 59: 2325-2334, Jun. 1, 2001.
Salazar et al., "Mesenchymal stem cells produce Wnt isoforms and TGF-beta1 that mediate proliferation and procollagen expression by lung fibroblasts," *Am J Physiol Lung Cell Mol Physiol.*, 297(5):L1002-L1011, Epub Sep. 4, 2009.
Santilli et al., "Transarterial wall oxygen gradients at a prosthetic vascular graft to artery anastomosis in the rabbit," *J Vasc Surg.*, 31(6):1229-1239, Jun. 2000.
Shay-Salit et al., "VEGF receptor 2 and the adherens junction as a mechanical transducer in vascular endothelial cells," *Proc Natl Acad Sci U S A.*, 99(14):9462-9467, Epub Jun. 21, 2002.
Shi et al., "[Effect of mesenchymal stem cells on cardiac function and restenosis of injured artery after myocardial infarction]." *Zhonghua Yi Xue Za Zhi.*, 91(32):2269-2273, Aug. 30, 2011 [Article in Chinese], English abstract only.
Swedberg et al. "Intimal fibromuscular hyperplasia at the venous anastomosis of PTFE grafts in hemodialysis patients. Clinical, immunocytochemical, light and electron microscopic assessment," *Circulation*, 80(6):1726-1736, Dec. 1989.
Tesch, "MCP-1/CCL2: a new diagnostic marker and therapeutic target for progressive renal injury in diabetic nephropathy," *Am J Physiol Renal Physiol.*, 294(4):F697-F701, Epub Feb. 13, 2008.
Wang et al., "Human mesenchymal stem cell transplantation changes proinflammatory gene expression through a nuclear factor-kappaB-dependent pathway in a rat focal cerebral ischemic model," *J Neurosci Res.*, 91(11):1440-1449, Epub Aug. 30, 2013.
Wang et al., "Venous stenosis in a pig arteriovenous fistula model—anatomy, mechanisms and cellular phenotypes," *Nephrol Dial Transplant.*, 23(2):525-533. Epub Nov. 23, 2007.
Wise et al., "Human mesenchymal stem cells alter macrophage phenotype and promote regeneration via homing to the kidney following ischemia-reperfusion injury," *Am J Physiol Renal Physiol.*, 306(10):F1222-F1235, Epub Mar. 12, 2014.
Yang et al. "The mouse arteriovenous fistula model," *J Vasc Interv Radiol.*, 20(7):946-950, Jul.
Yang et al., "Adventitial transduction of lentivirus-shRNA-VEGF-A in arteriovenous fistula reduces venous stenosis formation," *Kidney Int.*, 85(2):289-306, Epub Aug. 7, 2013, Print Feb. 2014.
Yang et al., Poster Abstract Presentations; Session Title: Poster Session III; Abstract 564: "Adventitial Human Mesenchymal Stem Cells Transplantation Reduces Venous Neointimal Hyperplasia in an Experimental Murine AVF Model," *Arterioscler Thromb Vasc Biol.*, 34(Suppl 1):A564, May 1, 2014.

\* cited by examiner

METHODS AND MATERIALS FOR REDUCING VENOUS NEOINTIMAL HYPERPLASIA OF AN ARTERIOVENOUS FISTULA OR GRAFT

CROSS-REFERENCE TO RELATED APPLICATIONS

This application claims the benefit of U.S. Provisional Application Ser. No. 62/166,241, filed May 26, 2015 and U.S. Provisional Application No. 62/147,762, filed Apr. 15, 2015. The disclosures of the prior applications are considered part of (and are incorporated by reference in) the disclosure of this application.

STATEMENT AS TO FEDERALLY SPONSORED RESEARCH

This invention was made with government support under HL098967 awarded by National Institutes of Health. The government has certain rights in the invention.

BACKGROUND

1. Technical Field

This document relates to methods and materials involved in reducing venous neointimal hyperplasia (VNH) of an arteriovenous fistula (AVF) or graft. For example, this document provides methods and materials for using stem cells (e.g., mesenchymal stem cells), extracellular matrix material, or a combination of stem cells and extracellular matrix material to reduce VNH of AVFs or grafts.

2. Background Information

In the United States, more than 350,000 patients with end-stage renal disease (ESRD) are being treated using hemodialysis. The maintenance of vascular access patency is essential for providing optimal hemodialysis in patients with ESRD. AVFs are the preferred manner for providing vascular access for hemodialysis. Only 60% of patients, however, have a functional AVF after one year. The major cause for AVF failure is VNH, which leads to the development of stenosis and subsequent thrombosis (Roy-Chaudhury et al., *Kidney International*, 59:2325-2334 (2001)).

SUMMARY

This document provides methods and materials for reducing VNH of an AVF or graft. For example, this document provides methods and materials for using stem cells (e.g., mesenchymal stem cells), extracellular matrix material, or a combination of stem cells and extracellular matrix material to reduce VNH of AVFs or grafts. As described herein, stem cells (e.g., adipose-derived mesenchymal stem cells) can be administered to the adventitia of the outflow vein to reduce the development of VNH associated with AVFs. As also described herein, extracellular matrix material (e.g., an extracellular matrix scaffold such as CorMatrix™) can be applied to (e.g., wrapped around) the adventitia of the outflow vein of AVFs to reduce the development of VNH associated with AVFs. Having the ability to reduce development of VNH of an AVF or graft using the methods and materials provided herein can allow clinicians and patients to maintain the function of AVFs or grafts whether involved in hemodialysis or other types of grafting procedures.

The methods and materials provided herein can be used to reduce the development of VNH after peripheral and coronary artery bypass graft surgery. In some cases, the methods and materials provided herein can be used in conjunction with angioplasty or stent placement. For example, stem cells (e.g., mesenchymal stem cells), extracellular matrix material, or both can be delivered using an endovascular catheter configured to target the adventitia. In some cases, the methods and materials provided herein can be used with endovascular delivery to the endothelium with or without using angioplasty, stents, or nanoparticles. In some cases, stem cells (e.g., mesenchymal stem cells) can be administered as described herein during angioplasty or stent placement. In some cases, extracellular matrix material can be applied to (e.g., wrapped around) the adventitia during or after a peripheral or coronary arterial bypass surgery.

In general, one aspect of this document features a method for reducing venous neointimal hyperplasia formation of an arteriovenous fistula or graft in a mammal. The method comprises, or consists essentially of, administering stem cells to an adventitia of a vein of the arteriovenous fistula or graft under conditions wherein venous neointimal hyperplasia formation of the arteriovenous fistula or graft is reduced. The mammal can be a human. The stem cells can be adipose-derived mesenchymal stem cells.

In another aspect, this document features a method for reducing venous neointimal hyperplasia formation of an arteriovenous fistula or graft in a mammal. The method comprises, or consists essentially of, applying extracellular matrix material to an adventitia of a vein of the arteriovenous fistula or graft under conditions wherein venous neointimal hyperplasia formation of the arteriovenous fistula or graft is reduced. The mammal can be a human. The extracellular matrix material can be porcine extracellular matrix material. The extracellular matrix material can be applied by wrapping the extracellular matrix material around the adventitia of the vein.

In another aspect, this document features a method for reducing venous neointimal hyperplasia formation of an arteriovenous fistula or graft in a mammal. The method comprises, or consists essentially of, (a) administering stem cells to an adventitia of a vein of the arteriovenous fistula or graft, and (b) applying extracellular matrix material to the adventitia, wherein venous neointimal hyperplasia formation of the arteriovenous fistula or graft is reduced. The mammal can be a human. The stem cells can be adipose-derived mesenchymal stem cells. The extracellular matrix material can be porcine extracellular matrix material. The extracellular matrix material can be applied by wrapping the extracellular matrix material around the adventitia of the vein.

In another aspect, this document features a method for reducing venous neointimal hyperplasia formation of an arteriovenous fistula in a mammal. The method comprises, or consists essentially of, implanting a stent comprising extracellular matrix material into a blood vessel of the arteriovenous fistula under conditions wherein venous neointimal hyperplasia formation of the arteriovenous fistula is reduced. The mammal can be a human. The extracellular matrix material can be porcine extracellular matrix material. The extracellular matrix material can be located between an inner wall of the blood vessel and an outer surface of the stent.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 4A is a representative section after Hematoxylin and eosin (H and E) staining in M transplanted or C vessels at day 7 after AVF placement. n is neointima, and m+a is media/adventitia. All are original magnification ×40. Bar is 50-mM. * is lumen. FIG. 4B is semiquantitative analysis revealing a significant increase in the average lumen vessel area of M transplanted vessels when compared to control C group for day 7 ($P<0.05$) and 21 ($P<0.05$). FIG. 4C is a semiquantitative analysis for the average area of the neointima/average area of the media/adventitia for both groups at day 7 and 21. By day 21, there was a significant decrease in the average area of the neointima/average area of the media/adventitia in the M transplanted vessels when compared to the C group ($P<0.05$). FIG. 4D is a semiquantitative analysis for the average cell density in the neointima for both groups at days 7 and 21. By day 7, the average cell density of the neointima in the M transplanted vessels was significantly lower than the C group ($P<0.0001$) and remained lower by day 21 ($P<0.05$). Each bar represents mean±SEM of 4-6 animals per group. Two-way ANOVA followed by Student t-test with post hoc Bonferroni's correction was performed. Significant differences among M transplanted and C vessels are indicated by $*P<0.05$ or $\#\#P<0.0001$.

FIG. 5A (upper panel) is the representative sections from TUNEL staining at outflow vein of the M transplanted and C vessels at day 7 and 21. Brown staining nuclei were positive for TUNEL. Negative control is shown where the recombinant terminal deoxynucleotidyl transferase enzyme was omitted. All are original magnification ×40. Bar is 50-mM. * is lumen. FIG. 5B is the semiquantitative analysis for TUNEL staining for M transplanted and C vessels at days 7 and 21. By day 7, the average density of cells staining positive for TUNEL (brown staining nuclei) at the outflow vein of M transplanted vessels was significantly higher than the C group ($P<0.0001$). By day 21, it remained significantly increased ($P<0.05$). FIG. 5A (lower panel) is representative sections after Ki-67 staining in outflow vessels removed mesenchymal stem cell transplanted vessels (M) or arteriovenous fistula alone (C) at day 7 after AVF placement. Brown staining nuclei are positive for Ki-67. IgG negative controls are shown. FIG. 5C is the semiquantitative analysis of Ki-67 staining at days 7 and 21. By day 7, there was a significant reduction in the average Ki-67 index in the M transplanted vessels when compared to C vessels ($P<0.0001$) and remained significantly lower by day 21 ($P<0.05$). Each bar represents mean±SEM of 4-6 animals. Two-way ANOVA followed by Student t-test with post hoc Bonferroni's correction was performed. Significant differences among M transplanted and C vessels are indicated by $*P<0.05$, $**P<0.001$, or $\#\#P<0.0001$.

FIG. 6A (upper panel) is the representative sections after FSP-1 staining in the venous stenosis of the M transplanted and C vessels at days 7 and 21. Brown staining cells are positive for FSP-1. IgG negative controls are shown. All are original magnification ×40. Bar is 50-mM. * is lumen. FIG. 6B is the semiquantitative analysis of FSP-1 staining for M transplanted and C vessels at days 7 and 21. By day 7, the average density of cells staining positive for FSP-1 at the outflow vein of M transplanted vessels was significantly lower than the C group ($P<0.001$). By day 21, it remained significantly increased ($P<0.01$). FIG. 6A (lower panel) is the representative sections after α-SMA staining in the venous stenosis of the M transplanted and C vessels at days 7 and 21. Brown staining cells are positive for α-SMA. FIG. 6C is the semiquantitative analysis of α-SMA staining for M transplanted and C vessels at days 7 and 21. By day 21, the average density of cells staining positive for α-SMA at the outflow vein of M transplanted vessels was significantly lower than the C group ($P<0.05$). Each bar represents mean±SEM of 4-6 animals per group. Two-way ANOVA followed by Student t-test with post hoc Bonferroni's correction was performed. Significant differences among M transplanted and C vessels are indicated by $*P<0.05$, $\#P<0.01$, or $\#\#P<0.0001$.

FIG. 7A (upper panel) is the representative sections after HIF-1α staining in the venous stenosis of the M transplanted and C vessels at days 7 and 21. Brown staining nuclei were positive for HIF-1α. IgG negative controls are shown. All are original magnification ×40. Bar is 50-mM. * is lumen. FIG. 7B is the semiquantitative analysis of HIF-1α staining for M transplanted and C vessels at days 7 and 21. By day 7, the average density of cells staining positive for HIF-1α at the outflow vein of M transplanted vessels was significantly lower than the C group ($P<0.0001$). By day 21, it remained significantly increased ($P<0.0001$). FIG. 7A (lower panel) is the representative sections after CD68 staining in the venous stenosis of the M transplanted and C vessels at days 7 and 21. Brown staining cells are positive for CD68. FIG. 7C is the semiquantiative analysis of CD68 staining for M transplanted and C vessels at days 7 and 21. By day 7, the average density of cells staining positive for CD68 at the outflow vein of M transplanted vessels was significantly lower than the C group ($P<0.05$). Each bar represents mean±SEM of 4-6 animals per group. Two-way ANOVA followed by Student t-test with post hoc Bonferroni's correction was performed. Significant differences among M transplanted and C vessels is indicated by $*P<0.05$ or $\#\#P<0.0001$.

FIG. 8A is a representative section after Hematoxylin and eosin (H and E) staining in scaffold (S) wrapped or control (C) vessels at day 7 after AVF placement. n is neointima, and m+a is media/adventitia. All were original magnification ×40. Bar is 50-mM. * is lumen. FIG. 8B is a semi-quantitative analysis that shows a significant increase in the average lumen vessel area of S wrapped vessels when compared to control C group for day 21 ($P<0.0001$). FIG. 8C is a semiquantitative analysis for the average area of the neointima for both groups at day 7 and 21. By day 7, there was a significant decrease in the average area of the neointima of the S wrapped vessels when compared to the C group ($P<0.05$). FIG. 8D is a semi-quantitative analysis for the average cell density in the neointima for both groups at days 7 and 21. By day 21, the average cell density of the neointima in the S wrapped vessels was significantly lower than the C group ($P<0.0001$). Each bar represents mean±SEM of 4-6 animals per group. Two-way ANOVA followed by Student t-test with post hoc Bonferroni's correction was performed. Significant differences among S wrapped and C vessels is indicated by $*P<0.05$ or $\#\#P<0.0001$.

FIG. 9A (upper panel) is the representative sections from TUNEL staining at outflow vein of the S wrapped and C vessels at day 7 and 21. Brown staining nuclei are positive for TUNEL. Negative control is shown where the recombinant terminal deoxynucleotidyl transferase enzyme was omitted. All are original magnification ×40. Bar is 50-mM. * is lumen. FIG. 9B is the semiquantitative analysis for TUNEL staining for S wrapped and C vessels at days 7 and 21. By day 7, the average density of cells staining positive for TUNEL (brown staining nuclei) at the outflow vein of S wrapped vessels was significantly higher than the C group ($P<0.0001$). By day 21, it remained significantly increased ($P<0.0001$). FIG. 9A (lower panel) is representative sections after Ki-67 staining in outflow vessels removed S wrapped vessels or arteriovenous fistula alone (C) at day 7 after AVF placement. Brown staining nuclei are positive for Ki-67. IgG negative controls are shown. FIG. 9C is the semiquantitative analysis of Ki-67 staining at days 7 and 21. By day 7, there was a significant reduction in the average Ki-67 index in the S wrapped vessels when compared to C vessels ($P<0.01$). Each bar represents mean±SEM of 4-6 animals. Two-way ANOVA followed by Student t-test with post hoc Bonferroni's correction was performed. Significant differences among S wrapped and C vessels are indicated by $\#P<0.01$ or $\#\#P<0.0001$.

FIG. 10A (upper panel) is the representative sections after α-SMA staining in the venous stenosis of the S wrapped and C vessels at days 7 and 21. Brown staining cells are positive for α-SMA. IgG negative controls are shown. All are original magnification ×40. Bar is 50-mM. * is lumen. FIG. 10B is the semiquantitative analysis of α-SMA staining for S wrapped and C vessels at days 7 and 21. By day 21, the average density of cells staining positive for α-SMA at the outflow vein of S wrapped vessels was significantly lower than the C group ($P<0.01$). FIG. 10A (lower panel) is the representative sections after FSP-1 staining in the venous stenosis of the S wrapped and C vessels at days 7 and 21. Brown staining cells are positive for FSP-1. FIG. 10C is the semiquantitative analysis of FSP-1 staining for S wrapped and C vessels at days 7 and 21. By day 7, the average density of cells staining positive for FSP-1 at the outflow vein of S wrapped vessels was significantly lower than the C group ($P<0.01$). By day 21, it remained significantly increased ($P<0.0001$). Each bar represents mean±SEM of 4-6 animals per group. Two-way ANOVA followed by Student t-test with post hoc Bonferroni's correction was performed. Significant differences among S wrapped and C vessels are indicated by $\#P<0.01$, or $\#\#P<0.0001$.

FIG. 11A (upper panel) is the representative sections after HIF-1α staining in the venous stenosis of the S wrapped and C vessels at days 7 and 21. Brown staining nuclei are positive for HIF-1α. IgG negative controls are shown. All are original magnification ×40. Bar is 50-mM. * is lumen. FIG. 11B is the semiquantitative analysis of HIF-1α staining for S wrapped and C vessels at days 7 and 21. By day 7, the average density of cells staining positive for HIF-1α at the outflow vein of S wrapped vessels was significantly lower than the C group ($P<0.0001$). By day 21, it remained significantly increased ($P<0.0001$). FIG. 11A (lower panel) is the representative sections after CD68 staining in the venous stenosis of the S wrapped and C vessels at days 7 and 21. Brown staining cells are positive for CD68. FIG. 11C is the semiquantiative analysis of CD68 staining for S wrapped and C vessels at days 7 and 21. By day 7, the average density of cells staining positive for CD68 at the outflow vein of S wrapped vessels was significantly lower than the C group ($P<0.05$). Each bar represents mean±SEM of 4-6 animals per group. Two-way ANOVA followed by Student t-test with post hoc Bonferroni's correction was performed. Significant differences among S wrapped and C vessels are indicated by $*P<0.05$ or $\#\#P<0.0001$.

DETAILED DESCRIPTION

Figure 1:
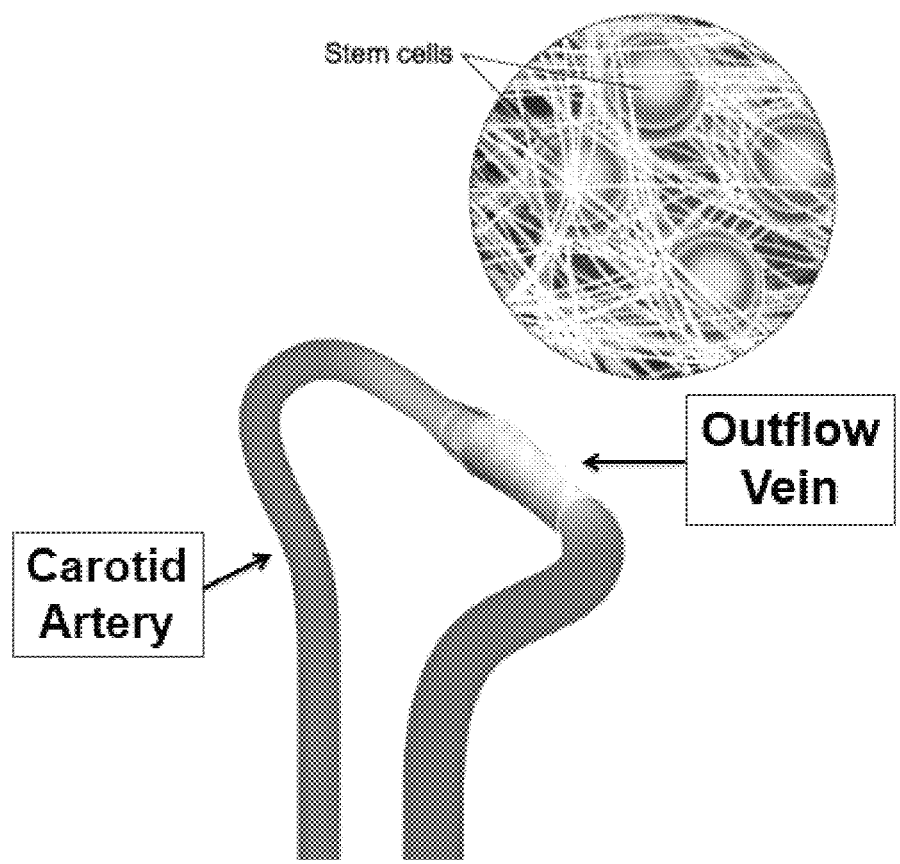
FIG. 1 is a schematic diagram of AVF placement with MSC.

This document provides methods and materials for reducing VNH formation of an AVF or graft. For example, this document provides methods and materials for using stem cells to reduce VNH formation of AVFs or grafts. As described herein, administering stem cells to the adventitia of a vein of an AVF or graft of a mammal can reduce VNH formation as compared to the level of VNH formation observed in a control mammal not receiving the stem cells. In addition, applying an extracellular matrix material to the adventitia of a vein of an AVF or graft (e.g., wrapping an extracellular matrix scaffold around the adventitia) can reduce VNH formation as compared to the level of VNH formation observed in a control mammal not receiving the extracellular matrix material. In some cases, both administering stem cells to the adventitia and applying an extracellular matrix material can be used to reduce VNH formation of AVFs or grafts as compared to the level of VNH formation observed in a control mammal not receiving the stem cells or the extracellular matrix material.

Any appropriate mammal having an AVF or graft can be treated as described herein. For example, humans, monkeys, dogs, cats, horses, cows, pigs, sheep, rats, and mice having an AVF or graft can be receive stem cells and/or extracellular matrix material as described herein to reduce VNH formation of the AVF or graft.

Examples of stem cells that can be used as described herein include, without limitation, mesenchymal stem cells such as adipose-derived mesenchymal stem cells, bone marrow-derived mesenchymal stem cells, umbilical cord tissue-derived mesenchymal stem cells, and placental derived mesenchymal stem cells. Examples of extracellular matrix material that can be used as described herein include, without limitation, porcine extracellular matrix material such as CorMatrix™ (material manufactured by Cook Biotech (West Lafayette, Ind.) for CorMatrix Cardiovascular, Inc. (Atlanta, Ga.)) and extracellular matrix material derived from plants, mice, rats, rabbits, cows, dogs, monkey, sheep, or baboons.

Any appropriate number of stem cells (e.g., adipose-derived mesenchymal stem cells) can be administered to the adventitia of a vein of an AVF or graft. For example, between about $1 \times 10^6$ and $1 \times 10^{12}$ stem cells (e.g., adipose-derived mesenchymal stem cells) can be injected into the adventitia of a vein of an AVF or graft. In some cases, a single administration can be performed to reduce VNH formation of AVFs or grafts. In some cases, multiple administrations can be performed to reduce VNH formation of AVFs or grafts. For example, stem cells (e.g., adipose-derived mesenchymal stem cells) can be injected two, three, four, five, six, or more times to reduce VNH formation of AVFs or grafts.

Any appropriate method can be used to apply extracellular matrix material to the adventitia of a vein of an AVF or graft. For example, extracellular matrix material in the form of a strip or sheet can be wrapped partially (e.g., at least about 25 percent around, at least about half way around, or at least about 75 percent around) or completely around the adventitia of a vein of an AVF or graft.

In some cases, the ability of stem cells, extracellular matrix material, or both to reduce VNH formation of AVFs or grafts can be monitored. Any method can be used to determine whether or not VNH formation is reduced. For example, ultrasound, intravascular ultrasound, angiogram, computed tomographic analysis, or magnetic resonance angiography can be used to assess possible VNH formation.

In some cases, stem cells, extracellular matrix material, or both can be applied to a stent. For example, a stent can be coated with extracellular matrix material and implanted into a blood vessel of a mammal. In some cases, extracellular matrix material can be applied to a stent in a manner such that drugs (e.g., anti-vascular endothelial growth factor-A or calcitriol), viruses (e.g., engineered lentiviruses or adenoviruses), small molecule inhibitors, and/or anti-miRNAs are delivered to a mammal. For example, a stent can be coated with extracellular matrix material that contains a drug (e.g., anti-vascular endothelial growth factor-A or calcitriol), virus (e.g., an engineered lentivirus or adenovirus), a small molecule inhibitor, and/or an anti-miRNA. Such a coated stent can be implanted into a blood vessel of a mammal to deliver the drug, virus, a small molecule inhibitor, and/or an anti-miRNA to the mammal. In some cases, the outer surface of a stent can include extracellular matrix material. In such cases, upon deployment of the stent into a blood vessel, the extracellular matrix material can be located between an inner wall of the blood vessel and an outer surface of the stent. In some cases, all the surfaces of an implanted stent can be coated with extracellular matrix material.

In some cases, a stent coated with stem cells, extracellular matrix material, or both as described herein can be implanted into a blood vessel of an AVF. For example, stent coated with an extracellular matrix material (e.g., an extracellular matrix material containing a drug, virus, a small molecule inhibitor, and/or an anti-miRNA) can be implanted into a blood vessel of an AVF to reduce VNH.

The invention will be further described in the following examples, which do not limit the scope of the invention described in the claims.

EXAMPLES

Example 1—Human Adipose Derived Mesenchymal Stem Cell Transplantation to the Adventitia of the Outflow Vein Attenuates VNH Associated with AVFs Experimental Animals Animals were housed at 22° C. temperature, 41% relative humidity, and 12-/12-hour light/dark cycles. Animals were allowed access to water and food ad libitum. CD1-Foxn1nu mice weighting 20-25 g and ages approximately 6-8 weeks were purchased from the Charles River Laboratories (Wilmington, Mass.). These animals lack a thymus, are unable to produce T cells, and are therefore immunodeficient which is ideal for xenograft research. Anesthesia was achieved with intraperitoneal injection of a mixture of ketamine hydrochloride (0.1-0.2 mg/g) and xylazine (0.02 mg/g). Arteriovenous fistula (AVF) between right carotid artery to the ipsilateral jugular vein was created as described elsewhere (Yang et al., *J. Vasc. Interv. Radiol.*, 20:946-950 (2009)). $2.5 \times 10^5$ MSC cells stably labeled with GFP in 5-μL of media were injected into the adventitia of the outflow vein at the time of AVF creation in the MSC group. Animals were sacrificed at day 7 following AVF placement for real time polymerase chain reaction (qRT-PCR) and histomorphometric analyses and at day 21 for histomorphometric analysis only.

Human MSCs Preparation

Human MSCs from healthy donors were obtained from the Human Cellular Therapy Laboratory. These cells were characterized with respect to surface markers and described elsewhere (Crespo-Diaz et al., *Cell Transplant*, 20:797-811 (2011)). Briefly, they are CD73 (+), CD90 (+), CD105 (+), CD44 (+), and HLA-ABC (+).

GFP Transfection

MSCs were transfected with GFP lentivirus. MSCs were grown in media containing the GFP lentivirus overnight. The media was changed to complete growth media the next day, and cells were checked for fluorescence after 48 hours. Once fluorescence was confirmed, the cells were cultured in complete media containing 1 μg/mL puromycin. Cells containing the plasmid were expanded in complete growth media.

$^{89}$Zr Labeling and in vivo Tracking of Stem Cells

Noninvasive PET imaging was used to evaluate the biodistribution of MSCs delivered to the adventitia outside the AVF in CD1-Foxn1nu mice. For this, MSCs were labeled with a biostable radiolabeling synthon, $^{89}$Zr-desferrioxamine-N-chlorosuccinimide, as described elsewhere (Bansal et al., *EJNMMI Res.*, 5:19 (2015)). After delivery of 2×10$^5$ 89Zr-labeled MSCs (at a radioactivity concentration of approximately 0.55 MBq per 10$^6$ cells) into the adventitia, the $^{89}$Zr-labeled MSCs were tracked for 3 weeks by using a small-animal PET/radiography system (Genesys4; Sofie BioSystems, Culver City, Calif.). In the control group, 0.28 MBq of $^{89}$Zr (HPO$_4$)$_2$ was delivered into the adventitia. PET images were normalized to units of standardized uptake value, which was calculated as follows: tissue radioactivity concentration/(injected dose/body weight in grams).

Immunohistochemistry

After fixation with formalin and processing, the samples were embedded in paraffin. Histological sectioning began at the outflow vein segment. Routinely, 80 to 120, 5-µm sections were obtained, and the cuff used to make the anastomosis could be visualized. Every 25-µm, 2-4 sections were stained with Hematoxylin and eosin, Ki-67, α-SMA, HIF-1α, or CD68, or TUNEL was performed on the paraffin-embedded sections from the outflow vein. The EnVision (DAKO, Carpinteria, Calif.) method was used with a heat-induced antigen retrieval step (Misra et al., *Kidney International*, 68:2890-2900 (2005)). The following antibodies were used: mouse monoclonal antibody Ki-67 (DAKO, 1:400) or rabbit polyclonal antibody to mouse for CD68, α-SMA, or HIF-1α (Abcam, 1:600). IgG antibody staining was performed to serve as controls.

TUNEL Staining

TUNEL staining was performed on paraffin-embedded sections from the outflow vein of MSC with scaffold (e.g., CorMatrix™) as specified by the manufacturer (DeadEnd Colorimetric tunnel assay system, G7360, Promega). Negative control is shown where the recombinant terminal deoxynucleotidyl transferase enzyme was omitted.

Morphometry and Image Analysis

Five-µm paraffin embedded sections were immunostained and quantified as described elsewhere (Yang et al., *Kidney International*, 85:289-306 (2014)).

RNA Isolation

The outflow vein was isolated and stored in RNA stabilizing reagent (Qiagen, Gaithersburg, Md.) as per the manufactures guidelines. To isolate the RNA, the specimens were homogenized, and total RNA from the samples was isolated using RNeasy mini kit (Qiagen) (Yang et al., *J. Vasc. Interv. Radiol.*, 20:946-950 (2009)).

Real Time Polymerase Chain Reaction (qRT-PCR) Analysis

Expression for the gene of interest was determined using qRT-PCR analysis as described elsewhere (Yang et al., *J. Vasc. Interv. Radiol.*, 20:946-950 (2009)). Primers used are shown in Table 1.

TABLE 1

Mouse primers used

| Gene | Sequence | SEQ ID NO: |
|---|---|---|
| MCP-1 | 5'-GGAGAGCTACAAGAGGATCAC-3' (sense) | 1 |
| | 5'-TGATCTCATTTGGTTCCGATCC-3' (antisense) | 2 |
| iNOS | 5'-TTGCTCATGACATCGACCAG-3' (sense) | 3 |
| | 5'-ACATCAAAGGTCTCACAGGC-3' (antisense) | 4 |

TABLE 1-continued

Mouse primers used

| Gene | Sequence | SEQ ID NO: |
|---|---|---|
| Arg-1 | 5'-CCCAGATGTACCAGGATTCTC-3' (sense) | 5 |
| | 5'-AGCTTGTCTACTTCAGTCATGG-3' (antisense) | 6 |
| 18S | 5'-GTTCCGACCATAAACGATGCC-3' (sense) | 7 |
| | 5'-TGGTGGTGCCCTTCCGTCAAT-3' (antisense) | 8 |

Statistical Methods

Data were expressed as mean±SEM. Multiple comparisons were performed with two-way ANOVA followed by Student t-test with post hoc Bonferroni's correction. Significant difference from control value was indicated by *$P<0.05$, #$P<0.01$, **$P<0.001$, or ##$P<0.0001$. JMP version 9 (SAS Institute Inc., Cary, N.C.) was used for statistical analyses.

Results

Surgical Outcomes

Forty-seven male B6.Cg-Foxn1nu/J mice underwent the placement of carotid artery to jugular vein fistula as described elsewhere (Janardhanan et al., *Kidney International*, August:338-352 (2013); Yang et al., *Kidney International*, 85:289-306 (2014); and Yang et al., *J. Vasc. Interv. Radiol.*, 20:946-950 (2009)). Eleven mice died after cell transplantation. 2×10$^5$ MSCs labeled with GFP were injected into the adventitia of the outflow vein at the time of AVF creation (FIG. 1). Animals were sacrificed at day 7 for either histomorphometric or qRT-PCR analyses for each of the following groups: AVF only (C, n=6) and MSC (M, n=6). Another group of animals were sacrificed at day 21 after fistula placement for histomorphometric and immunohistochemical analyses for the following groups: AVF only (C, n=6) and MSC (M, n=6).

Localization of MSCs after Adventitial Delivery of to the Outflow Vein of AVF

Figure 2:
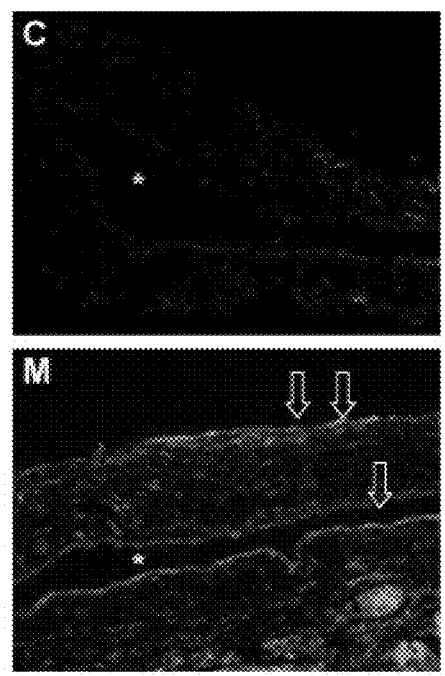
FIG. 2. Localization of human adipose derived mesenchymal stem cells (MSCs). $2.5 \times 10^5$ MSCs stable transfected with GFP were injected into the adventitia of the outflow vein of AVF at the time of creation. GFP labeled human adipose derived mesenchymal stem cells (MSCs) were present at day 7 in MSC transplanted vessels (M) compared to outflow vein vessels removed from control animals (C) after AVF placement. Nuclei are blue. There are GFP positive cells (arrows) in the vessel wall of the outflow vein at day 7. The lumen is marked with an *.

In order to assess the spatial and temporal localization of MSCs to the adventitia of the outflow vein, MSCs were stably transfected with GFP in order to track them. Confocal microscopy of the outflow vein after adventitial transplantation of MSC was performed at different times. This demonstrated that GFP positive cells from the M transplanted vessels (blue positive cells, FIG. 2, arrow head) were present at day 7. However, by day 21, there was no co-localization of the GFP signal from either group.

Figure 12:
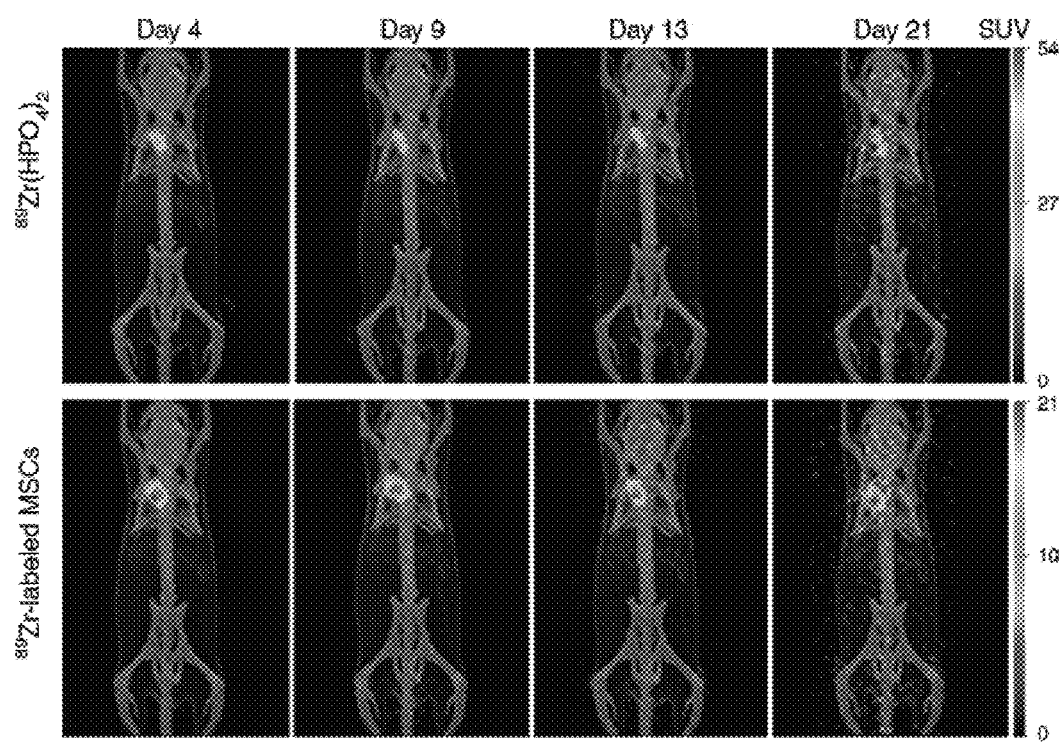
FIG. 12. Serial PET images of $^{89}Zr$ distribution in mice after adventitial delivery of $^{89}Zr$-labeled MSCs or $^{89}Zr$ $(HPO_4)_2$. The anatomic reference skeleton images were formed by using the mouse atlas registration system algorithm with information obtained from the stationary top-view planar x-ray projector and side-view optical camera. SUV=standardized uptake value.

PET images of mice after adventitial delivery of $^{89}$Zr-labeled MSCs revealed that more than 90% of administered $^{89}$Zr radioactivity was retained at the delivery site on day 4 (FIG. 12). Adventitial retention of $^{89}$Zr radioactivity cleared slowly from day 4 to day 21, losing approximately 20% over this period (FIG. 12). Most $^{89}$Zr radioactivity that was cleared from the adventitia appeared to translocate to bones. This result confirmed the results obtained using confocal microscopy with GFP-labeled cells on day 7. PET imaging of $^{89}$Zr-labeled MSCs allowed tracking of cells beyond 7 days, which was not possible with GFP-labeled cells. The retention of most of the delivered stem cells at the delivery site on day 21 demonstrates that the effect was longer than what was visualized using GFP labeling. In the case of the control group, in which $^{89}$Zr (HPO$_4$)$_2$ was administered, a biodistribution similar to that of $^{89}$Zr-labeled MSCs was seen, with most of the radioactivity (approximately 80%) retained at the delivery site and the rest redistributing to bones.

Adventitial Transplantation of MSC Reduces Gene Expression of Mcp-1

Figure 3:
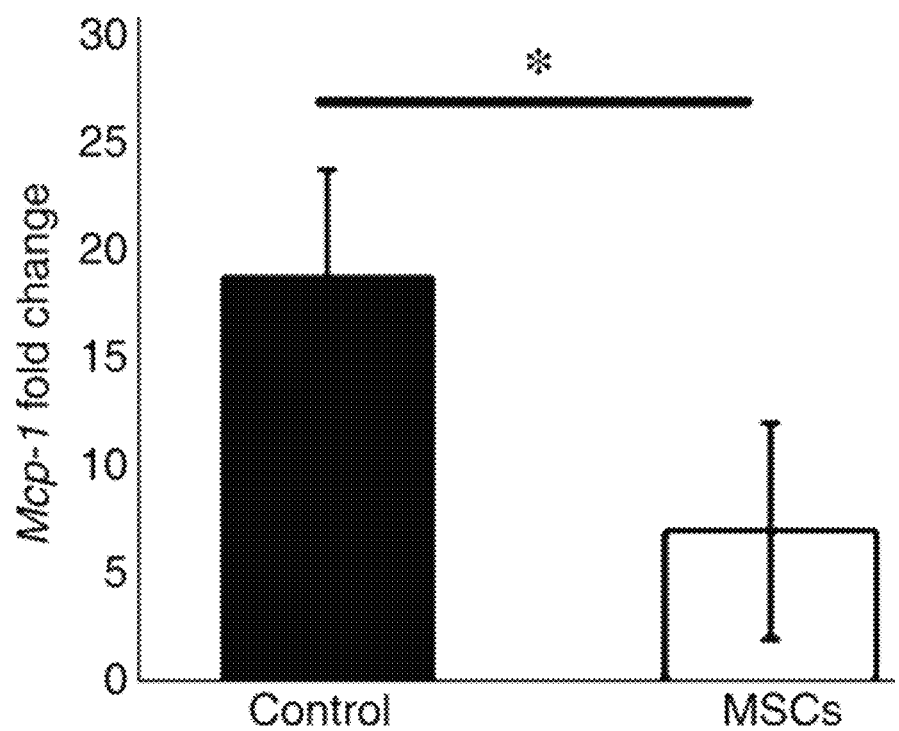
FIG. 3. Monocyte chemoattractant protein-1 (Mcp-1) gene expression at day 7 in MSC transplanted vessels (M) compared to outflow vein vessels removed from animals (C). There was a significant decrease in the mean Mcp-1 gene expression in the M transplanted vessels when compared to C group ($P<0.05$). Each bar shows the mean±SEM of 4-6 animals per group. Two-way ANOVA with Student t test was performed. Significant differences among M transplanted and C vessels are indicated by $*P<0.05$.

Studies demonstrated that MSCs exert their anti-inflammatory effect through a reduction in gene expression of Mcp-1 (Wise et al., *Am. J. Physiol. Renal Physiol.*, 306: F1222-1235 (2014)). The gene expression of Mcp-1 was assessed by performing qRT-PCR analysis at day 7 (FIG. 3A). M transplanted vessels were compared to control AVFs alone. The average gene expression of Mcp-1 at outflow vein of M transplanted vessels was significantly lower than the C group (average reduction: 70%, P<0.05).

Adventitial transplantation of MSC to the outflow vein reduced the average neointima area/media+adventitia area and cell density in the neointima while increasing the average lumen vessel area at days 7 and 21.

Figure 4:
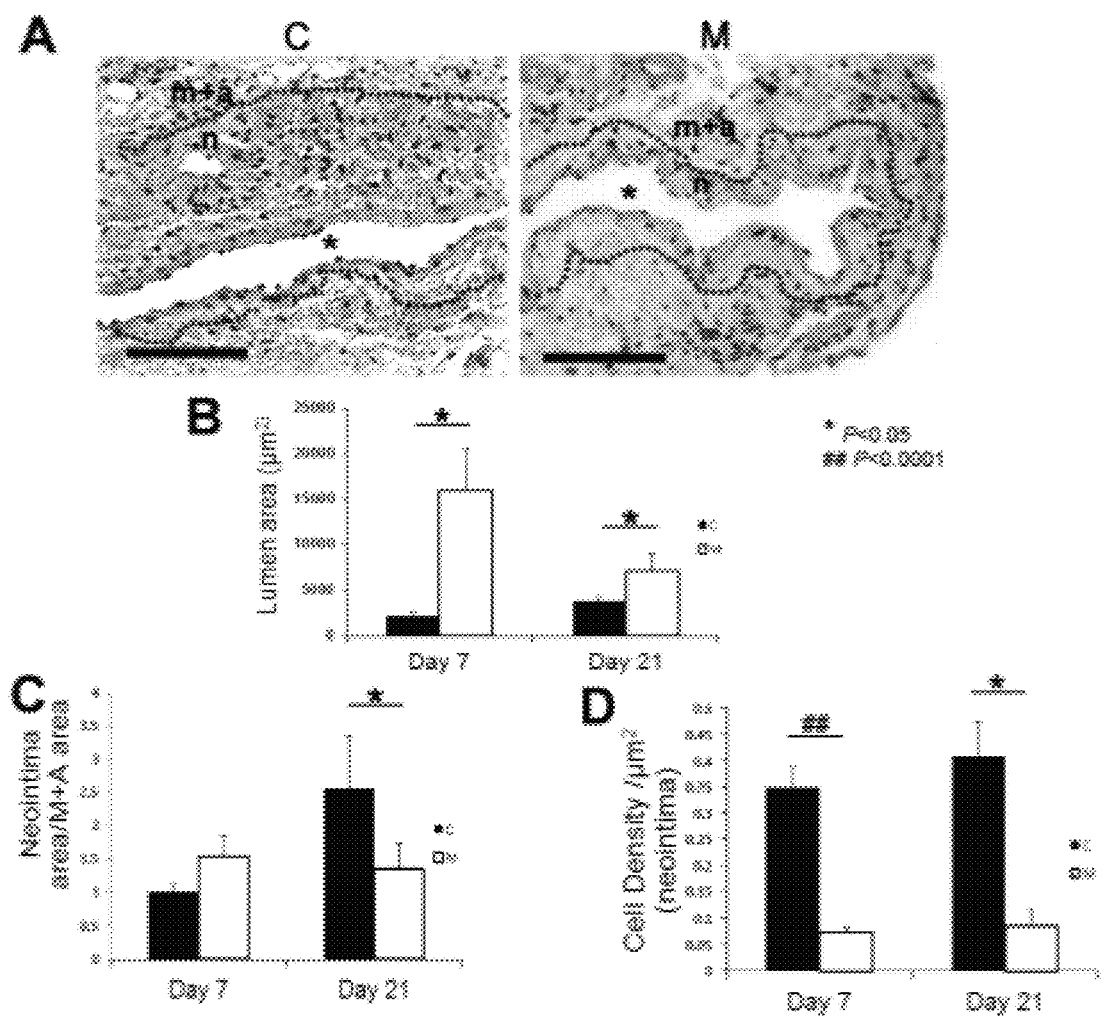
FIGS. 4A-D. Histomorphometric analysis of mesenchymal stem cell transplanted vessels (M) compared to outflow vein vessels removed from animals with AVF only (C) at day 7 and 21 after placement.

The vascular remodeling of the outflow vein in the M transplanted vessels and C vessels at day 7 and 21 was determined using histomorphometric analysis as described elsewhere (Janardhanan et al., *Kidney International*, August: 338-352 (2013); and Yang et al., *Kidney International*, 85:289-306 (2014)). By examining the Hematoxylin and eosin stained sections, one was able to differentiate between the neointima (n) and media/adventitia (m+a, FIG. 4A). The average lumen vessel area was determined at day 7 and a significant increase in the outflow vein removed from M transplanted vessels versus C group (average increase: 176%, P<0.001) was observed. By day 21, it remained significantly increased in the M transplanted vessels when compared to C group (average increase: 415%, P<0.0001). The average of the neointima area/media+adventitia area also was determined. By day 21, there was a significant decrease in the neointima area/media+adventitia area in the outflow vein removed from the M transplanted vessels when compared to the C group (average reduction: 77%, P<0.05, FIG. 4C).

Neointimal hyperplasia is characterized by cell proliferation, cell differentiation, and extra cellular matrix deposition (Roy-Chaudhury et al., *Kidney International*, 59:2325-2334 (2001); Rekhter et al., *Arterioscler. Thromb.*, 13:609-617 (1993); and Swedberg et al., *Circulation*, 80:1726-1736 (1989)). The cell density was determined to assess if reduction of neointimal area was caused by change in cell density. By day 7, the average cell density of the neointima in the M treated vessels was significantly lower than the C group (average reduction: 83%, P<0.0001, FIG. 4C). By day 21, it remained lower in the M transplanted vessels when compared to the C group (average reduction: 83%, P<0.0001, FIG. 4C).

Adventitial Transplantation of MSC to the Outflow Vein Increases TUNEL Staining

Figure 5:
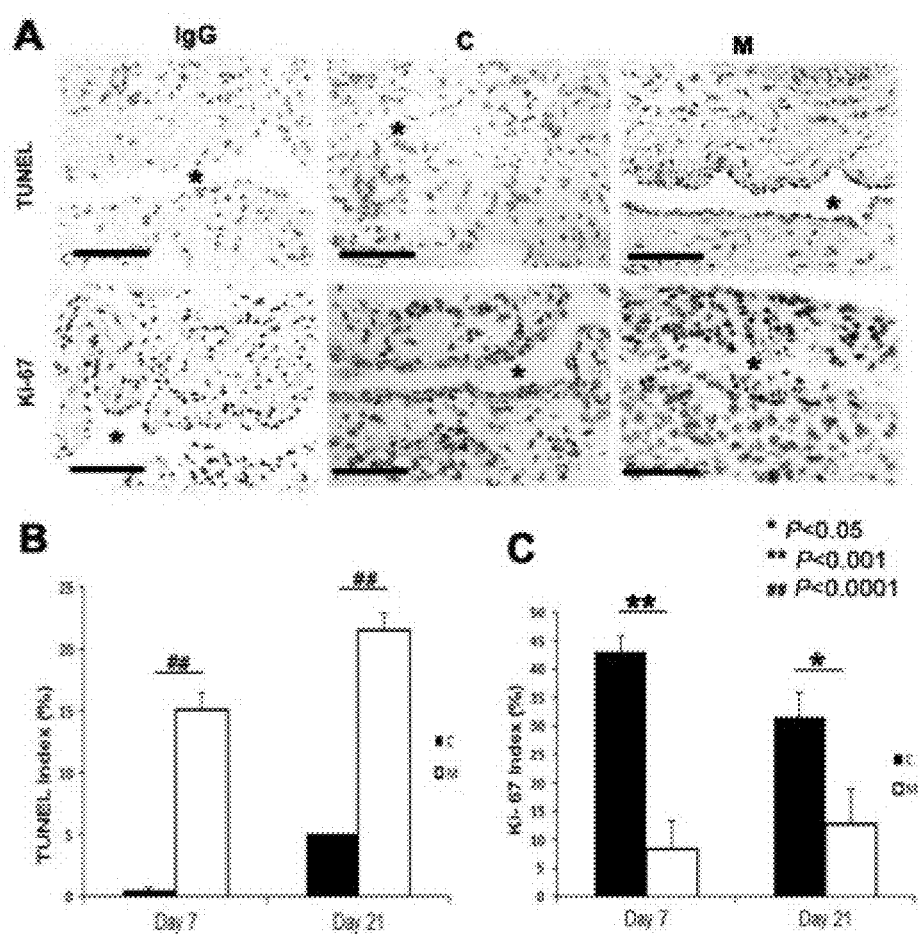
FIGS. 5A-C. TdT-mediated dNTP nick end labeling (TUNEL) staining and Ki-67 staining in murine AVF at day 7 and 21 after placement of AVF in outflow vein alone (C) and MSC transplanted vessels (M).

The decrease in cell density might be due to an increase in apoptosis (Shay-Salit et al., *Proc. Natl. Acad. Sci. USA*, 99:9462-9467 (2002)). Apoptosis was evaluated by using TUNEL staining (FIG. 5A, upper panel). By day 7, the average density of cells staining positive for TUNEL (brown staining nuclei) at the outflow vein of M transplanted vessels was significantly increased compared to the C group (average increase: 180%, P<0.0001). By day 21, it remained higher in the M transplanted vessels compared to the C group (average increase: 427%, P<0.0001). These results demonstrate that M transplanted vessels have increased TUNEL activity indicating cellular apoptosis when compared to C vessels.

Adventitial Transplantation of MSC to the Outflow Vein Reduces Cellular Proliferation at the Outflow Vein Ki-67 staining was used to assess a possible association between decreased cellular density and a reduction in cellular proliferation. Brown staining nuclei were positive for Ki-67 (FIG. 5A, lower panel). By seven days after fistula placement, there was a significant reduction in the average Ki-67 index in the M transplanted vessels when compared to C group (average reduction: 81%, P<0.001, FIG. 5C). By day 21, it remained significantly lower in the M transplanted vessels when compared to C vessels (average reduction: 60%, P<0.05).

Figure 6:
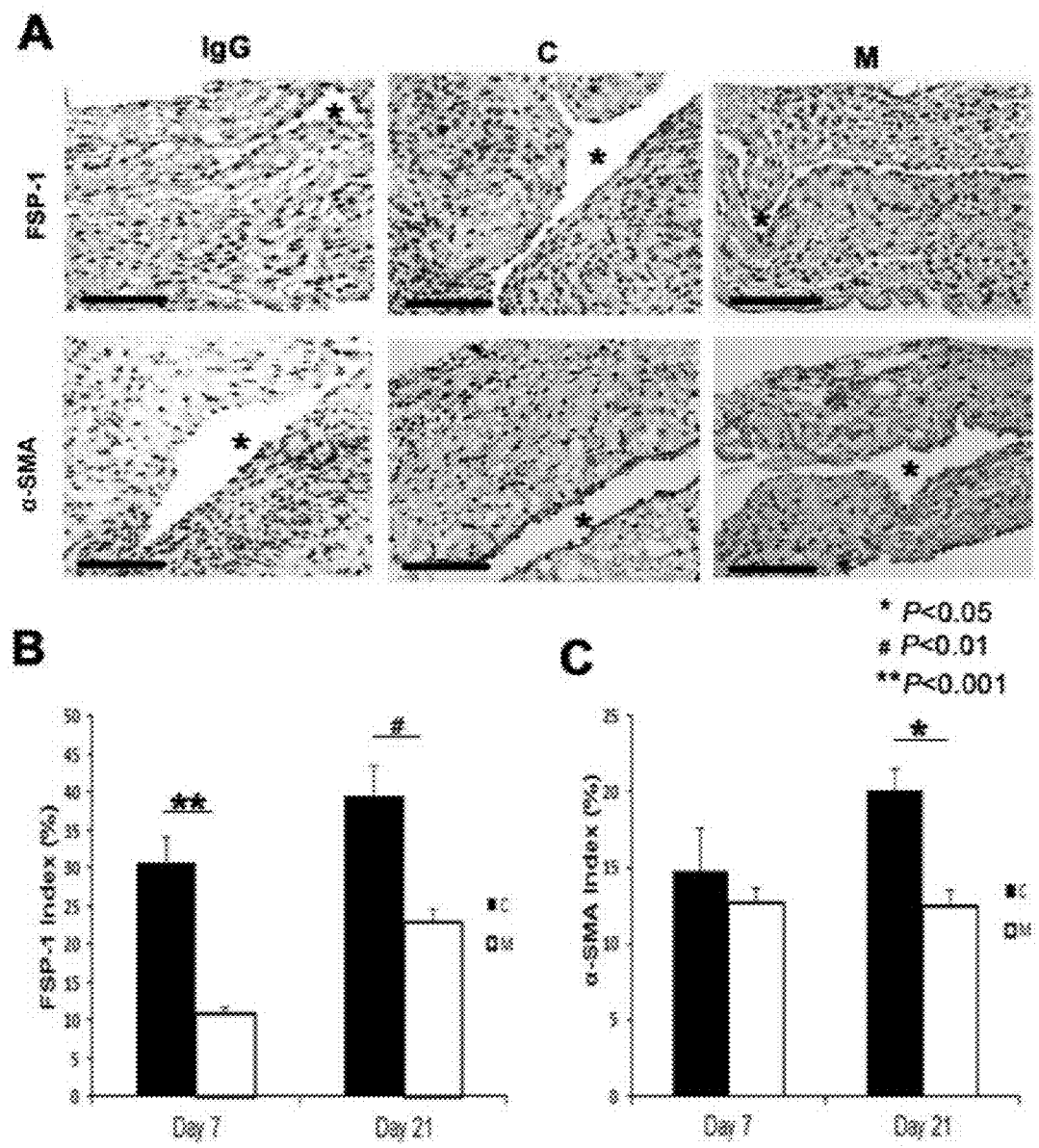
FIGS. 6A-C. Fibroblast specific protein-1 (FSP-1) and α-smooth muscle cell actin (α-SMA) staining in murine AVF at day 7 and 21 after placement of AVF in outflow vein alone (C) and MSC transplanted vessels (M).

Adventitial Transplantation of MSC to the Outflow Reduces α-SMA and FSP-1 Staining Fibroblast specific protein-1 (FSP-1) was used as a fibroblast marker (FIG. 6A, upper panel). Smooth muscle deposition was assessed using α-SMA staining (FIG. 6A, lower panel). Other studies implicated fibroblast to myofibroblast (α-SMA) differentiation resulting in VNH (Misra et al., *Kidney International*, 68:2890-2900 (2005); and Wang et al., *European Renal Association;* 23:525-533 (2008)). By day 7, a significant decrease in the average FSP-1 staining was observed in the M transplanted vessels when compared to C group (average reduction: 65%, P<0.001, FIG. 6B). By day 21, it remained significantly lower in the M transplanted vessels when compared to C group (average reduction: 42% P<0.01). By day 21, the average α-SMA staining was significantly lower in the M transplanted vessels when compared to C group (average reduction: 27%; P<0.05, FIG. 6C). Overall these results indicate that at day 7 there is a reduction in FSP-1 staining followed by a decrease in α-SMA staining by day 21 in M transplanted vessels when compared to C vessels.

Figure 7:
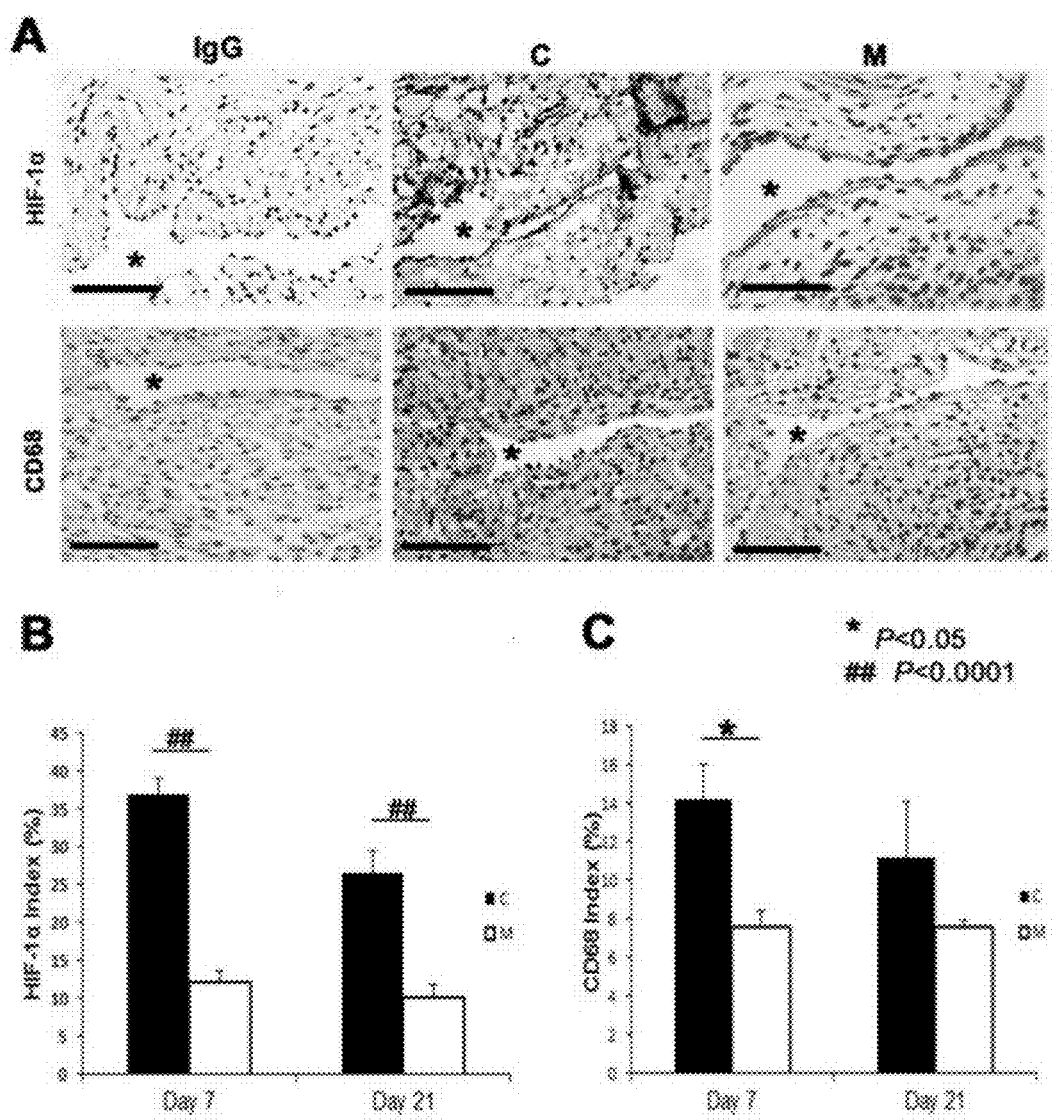
FIGS. 7A-C. HIF-1α and CD68 staining in murine AVF at day 7 and 21 after placement in outflow vein alone (C) and MSC transplanted vessels (M).

Adventitial Transplantation of MSC to the Outflow is Associated with a Reduction in HIF-1α Staining Other studies demonstrated increased HIF-1α expression in animal models of hemodialysis graft failure and in clinical specimens from patients with hemodialysis vascular access failure (Misra et al., *J. Vasc. Interv. Radiol.*, 21:1255-1261 (2010); and Misra et al., *J. Vasc. Interv. Radiol.*, 19:252-259 (2008)). HIF-1α staining was quantified to assess whether MSC transplantation had an effect on the expression of HIF-1α at the outflow vein of AVF. Brown staining nuclei were positive for HIF-1α (FIG. 7A, upper panel). By day 7, there was a significant reduction in the average density of HIF-1α staining M transplanted vessels when compared to C vessels (average reduction: 67%, P<0.0001). By day 21, it remained significantly lower in the M treated vessels when compared to C vessels (average reduction: 62%, P<0.0001). Overall these results indicate that there is decreased expression in HIF-1α in M transplanted vessels when compared to C treated vessels.

Adventitial Transplantation of MSC to the Outflow is Associated with a Reduction in CD68 Staining Other studies demonstrated increased CD68 expression (a marker for macrophages) in animal models of hemodialysis graft failure and in clinical specimens from patients with hemodialysis vascular access failure (Misra et al., *J. Vasc. Interv. Radiol.*, 21:1255-1261 (2010); and Misra et al., *J. Vasc. Interv. Radiol.*, 19:252-259 (2008)). CD68 staining was quantified to assess whether MSC transplantation had an effect on the expression of macrophage at the outflow vein of AVF. Cells staining brown in the cytoplasm were positive for CD68 (FIG. 7A, lower panel). By day 7, there was a significant reduction in the average density of CD68 staining in the M treated vessels when compared to C vessels (average reduction: 51%, P<0.05, FIG. 7C). Overall, there is a significant decrease in CD68 staining in the M transplanted vessels when compared to controls.

These results demonstrate that adventitial transplantation of human adipose derived MSCs to the outflow vein of AVF in a murine model reduces VNH. This is mediated by a significant decrease in the gene expression of Mcp-1 in the outflow vein transplanted with MSCs compared to controls at day 7. There was a significant increase in average TUNEL staining with a decrease in proliferation. In addition, there was a significant decrease in the FSP-1, CD68, and $\alpha$-SMA staining accompanied with a decrease in average HIF-1$\alpha$ staining.

Example 2—Wrapping an Extracellular Matrix Scaffold Around the Adventitia of the Outflow Vein of AVFs Attenuates VNH Experimental Animals Animals were housed at 22° C. temperature, 41% relative humidity, and 12-/12-hour light/dark cycles. Animals were allowed access to water and food ad libitum. CD1-Foxn1nu mice weighting 20-25 g and ages approximately 6-8 weeks were purchased from the Charles River Laboratories (Wilmington, Mass.). These animals lack a thymus, are unable to produce T cells, and are therefore immunodeficient which is ideal for xenograft research. Anesthesia was achieved with intraperitoneal injection of a mixture of ketamine hydrochloride (0.1-0.2 mg/g) and xylazine (0.02 mg/g). AVF between right carotid artery to the ipsilateral jugular vein was created as described elsewhere (Yang et al., *J. Vasc. Interv. Radiol.*, 20:946-950 (2009)). 1×4 mm CorMatrix™ scaffolds were wrapped around the outflow vein and sutured using 8-0 nylon to secure the scaffold to the outflow vein at the time of AVF creation (FIG. 1). Animals were sacrificed at day 7 and 21 for histomorphometric analyses for AVF only (C, n=6) or scaffold alone (S, n=6).

CorMatrix™ Scaffold Wrapped Around the Adventitia of the Outflow Vein of the AVF The scaffold (CorMatrix™) material was created by Cook Biotech (West Lafayette, Ind.) for CorMatrix Cardiovascular, Inc. (Atlanta, Ga.) and is composed of porcine small-intestine submucosa (SIS). Physically, the SIS was about 155-µm thick with pore sizes up to 50 µm when hydrated. The scaffolds were cut to 1×4-mm.

Immunohistochemistry

After fixation with formalin and processing, the samples were embedded in paraffin. Histological sectioning began at the outflow vein segment. 80 to 120, 5-µm sections were obtained, and the cuff used to make the anastomosis could be visualized. Every 0.1 mm, 2-4 sections were stained with Hematoxylin and eosin, Ki-67, $\alpha$-SMA, or HIF-1$\alpha$, or TUNEL was performed on paraffin-embedded sections from the outflow vein. The EnVision (DAKO, Carpinteria, Calif.) method was used with a heat-induced antigen retrieval step (Misra et al., *Kidney International*, 68:2890-2900 (2005)). The following antibodies were used: mouse monoclonal antibody Ki-67 (DAKO, 1:400) or rabbit polyclonal antibody to mouse for $\alpha$-SMA and HIF-1$\alpha$ (Abcam, 1:600). IgG antibody staining was performed to serve as controls.

TUNEL Staining

TUNEL staining was performed on paraffin-embedded sections from the outflow vein of Scaffold treated vessels and AVF only as specified by the manufacturer (DeadEnd Colorimetric tunnel assay system, G7360, Promega). Negative control is shown where the recombinant terminal deoxynucleotidyl transferase enzyme was omitted.

Morphometry and Image Analysis

Five-µm paraffin embedded sections were immunostained and quantified as described elsewhere (Yang et al., *Kidney International*, 85:289-306 (2014)).

Statistical Methods

Data were expressed as mean±SEM. Multiple comparisons were performed with two-way ANOVA followed by Student t-test with post hoc Bonferroni's correction. Significant differences from control value were indicated by *$P<0.05$ or #$P<0.01$. JMP version 9 (SAS Institute Inc., Cary, N.C.) was used for statistical analyses.

Results

Surgical Outcomes

Twenty-four male B6.Cg-Foxn1nu/J mice underwent the placement of carotid artery to jugular vein fistula as described elsewhere (Janardhanan et al., *Kidney International*, August:338-352 (2013); Yang et al., *Kidney International*, 85:289-306 (2014); and Yang et al., *J. Vasc. Interv. Radiol.*, 20:946-950 (2009)). Animals were sacrificed at day 7 and 21 for histomorphometric analyses for AVF only (C, n=6) or scaffold alone (S, n=6).

Figure 8:
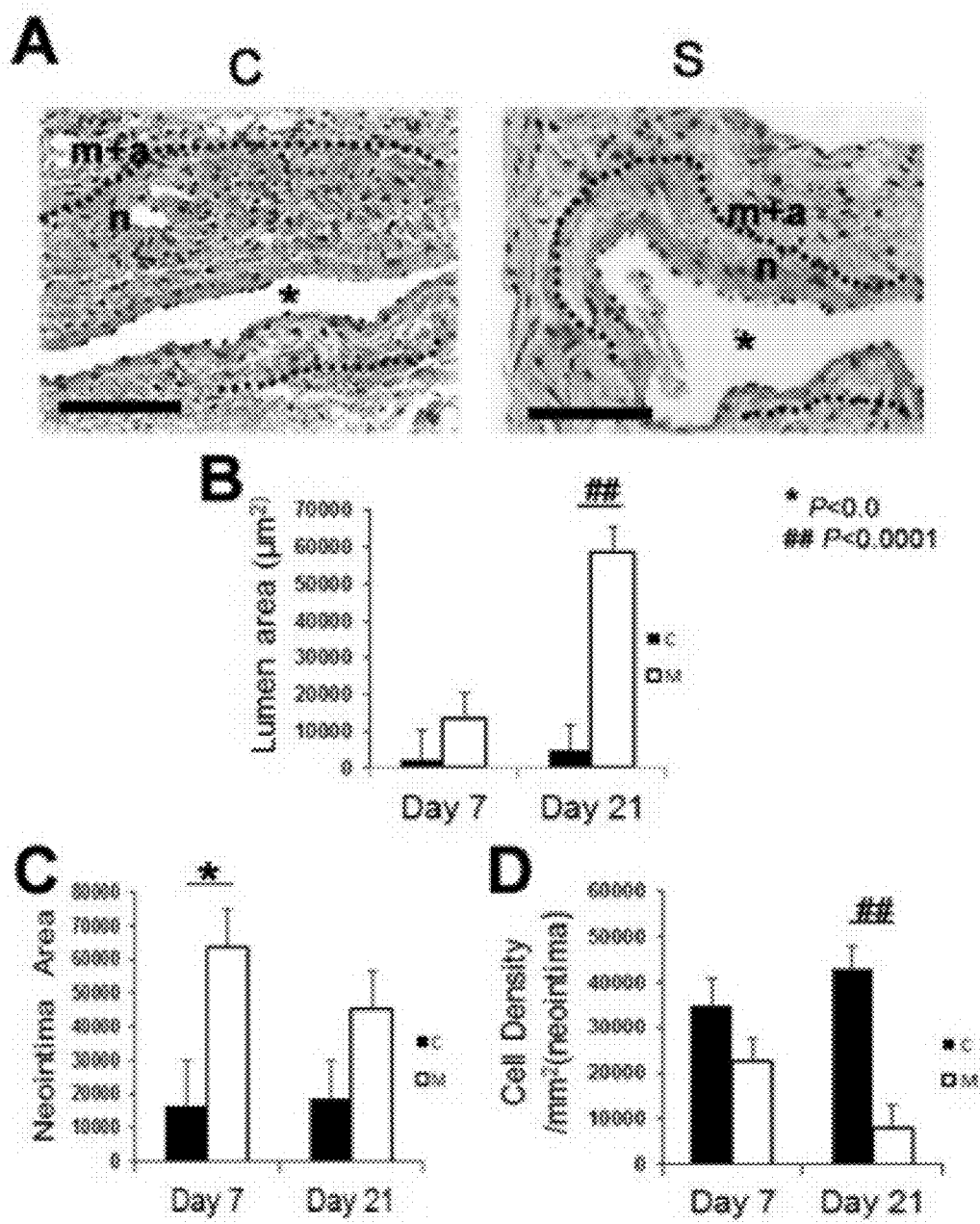
FIGS. 8A-D. Histomorphometric analysis in CorMatrix™ scaffold wrapped vessels (S) when compared to control AVF (C).

CorMatrix™ Wrapped Outflow Vein has Reduced Average Neointima Area and Cell Density with Increased Average Lumen Vessel Area The vascular remodeling of the outflow vein in the different groups at day 7 and 21 was determined using histomorphometric analysis as described elsewhere (Janardhanan et al., *Kidney International*, August:338-352 (2013); and Yang et al., *Kidney International*, 85:289-306 (2014)). Examining the Hematoxylin and eosin stained sections allowed for the differentiation between the neointima (n) and media/adventitia (m+a, FIG. 8A). By day 21, the average lumen vessel area was significantly increased in the outflow vein removed from the S treated vessels when compared to the C alone (average increase: 1800%, $P<0.0001$). The average area of the neointima was determined. By day 7, there was a significant decrease in the average area of the neointima in the outflow vein removed from the S treated vessels when compared to the C group (average reduction: 77%, $P<0.05$, FIG. 8B). By day 21, there was no difference between the two groups. Finally, the cell density was determined to assess if the reduction in neointimal area was caused by change in cell density. By day 21, the average cell density of the neointima in the S treated vessels was significantly lower than the C group (average reduction: 83%, $P<0.001$, FIG. 8C).

Figure 9:
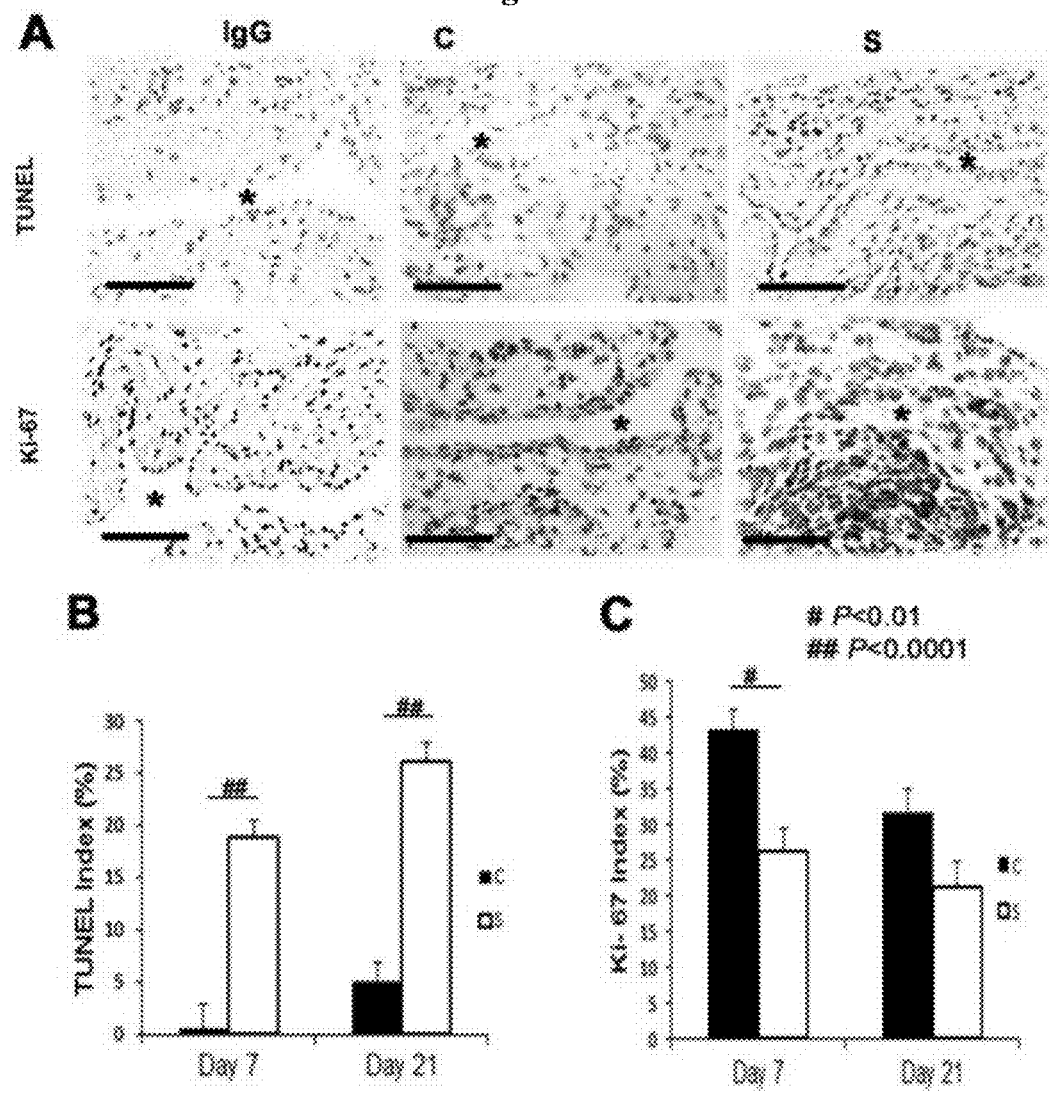
FIGS. 9A-C. TdT-mediated dNTP nick end labeling (TUNEL) and Ki-67 staining in CorMatrix™ scaffold wrapped vessels (S) when compared to control AVF (C).

CorMatrix™ Wrapped Outflow Vein has Increased TUNEL Staining when Compared to Control Vessels It is possible that the decrease in cell density also was due to an increase in apoptosis. Apoptosis was evaluated by using TUNEL staining (FIG. 9A, upper panel). By day 7, the average density of cells staining positive for TUNEL (brown staining nuclei) at the outflow vein of S treated group was significantly higher than the C treated group (average increase: 38200%, $P<0.0001$, FIG. 9B). By day 21, the average density of cells staining positive for TUNEL at the outflow vein of S treated group was significantly higher than the C treated group (average increase: 516%, $P<0.0001$).

CorMatrix™ Wrapped Outflow Vein has Reduced Cellular Proliferation when Compared to Control Vessels Because the cellular density was decreased, Ki-67 staining was performed to determine if this was associated with a reduction in cellular proliferation. Brown staining nuclei were positive for Ki-67 (FIG. 9A, lower panel). By 7 days after fistula placement, there was a significant reduction in the average Ki-67 staining in the S treated vessels when compared to C treated vessels (average reduction: 39%, P<0.0001, FIG. 9C). By day 21, there was no difference between the two groups.

Figure 10:
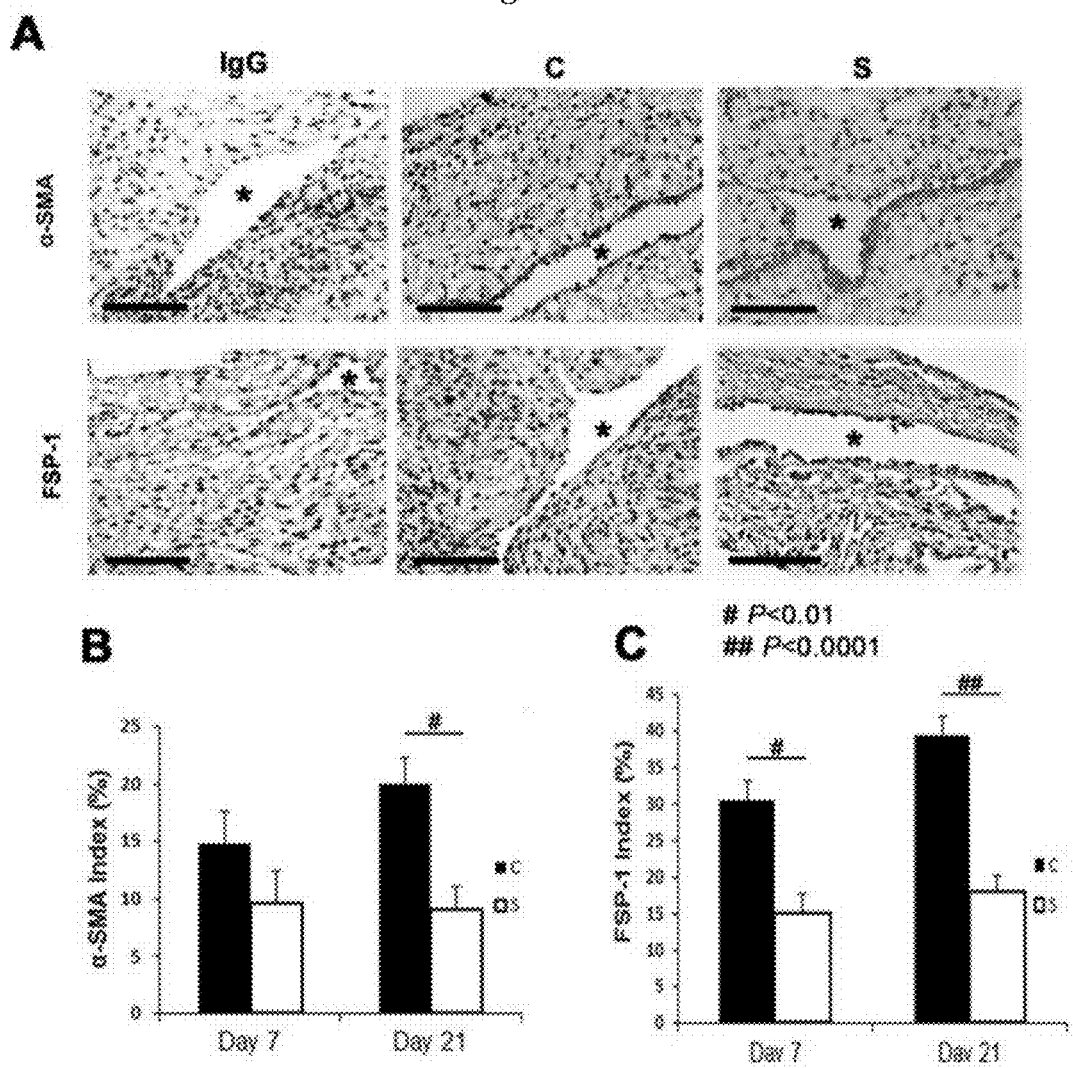
FIGS. 10A-C. α-SMA and FSP-1 staining in CorMatrix™ scaffold wrapped vessels (S) when compared to control AVF (C).

CorMatrix™ Wrapped Outflow Vein has Reduced α-SMA and FSP-1 Staining when Compared to Control Vessels Smooth muscle deposition was assessed using α-SMA staining (FIG. 10A, upper panel). There was no difference between the two groups at day 7, however, by day 21, the average α-SMA staining was significantly lower in the S treated vessels when compared to C group (average reduction: 55% P<0.05, FIG. 10B). FSP-1, a marker for fibroblasts, was used to identify the presence of such cells (FIG. 10A, lower panel). Other studies have implicated fibroblast to myofibroblast (α-SMA) differentiation as resulting in VNH (Misra et al., Kidney International, 68:2890-2900 (2005); and Wang et al., European Renal Association; 23:525-533 (2008)). By day 7, a significant decrease in the average FSP-1 staining was observed in the S treated vessels when compared to C group (average reduction: 55%, P<0.01, FIG. 10C). By day 21, the average FSP-1 staining remained significantly lower in the S treated vessels when compared to C group (average reduction: 55% P<0.001). Overall, these results indicate that at day 7 there was a reduction in FSP-1 staining followed by a decrease in α-SMA staining by day 21 in S treated vessels when compared to C vessels.

Figure 11:
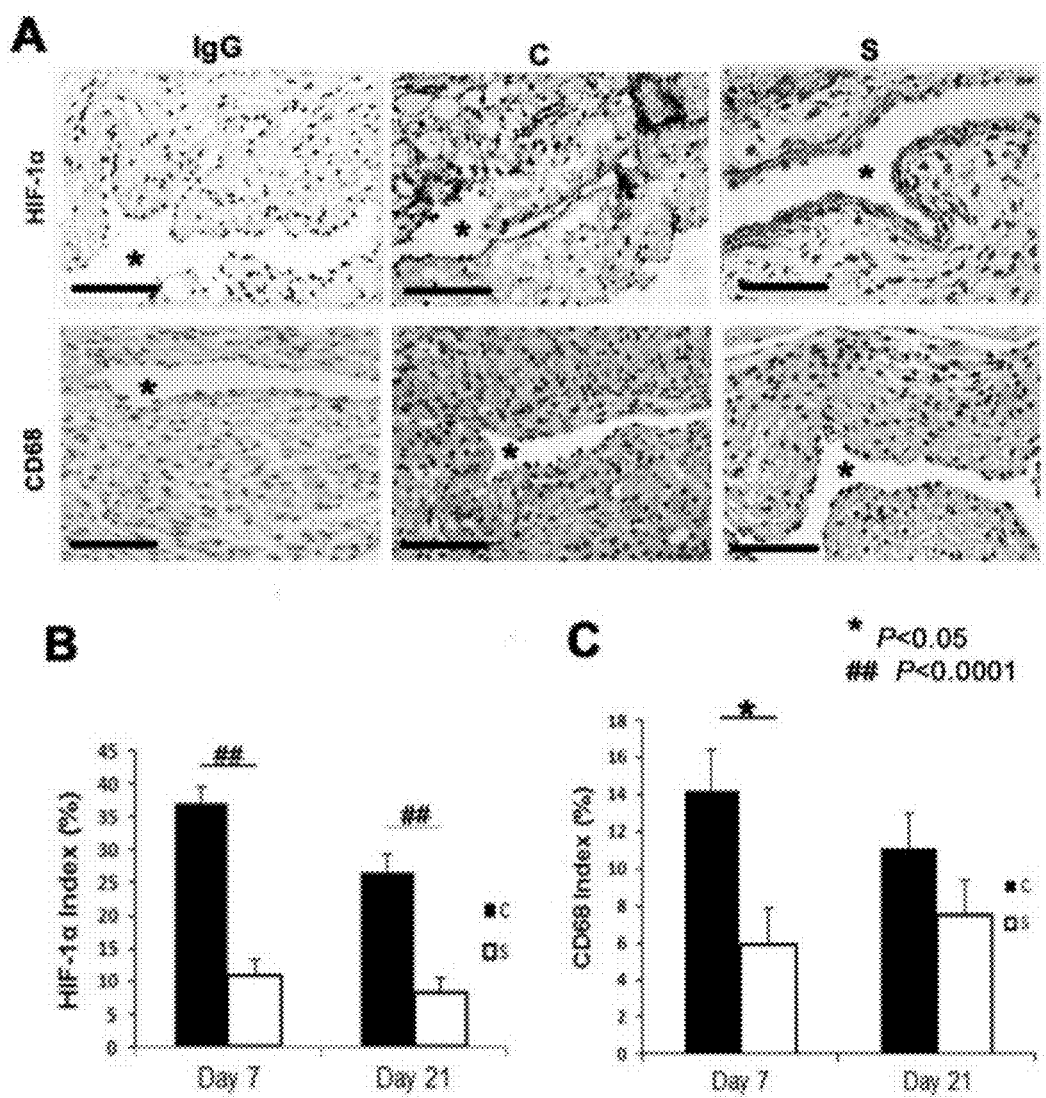
FIGS. 11A-C. HIF-1α and CD68 staining in CorMatrix™ scaffold wrapped vessels (S) when compared to control AVF (C).

CorMatrix™ Wrapped Outflow Vein has Reduced HIF-1α Staining when Compared to Control Vessels Other studies demonstrated increased HIF-1α expression in animal models of hemodialysis graft failure and in clinical specimens from patients with hemodialysis vascular access failure (Misra et al., J. Vasc. Interv. Radiol., 21:1255-1261 (2010); and Misra et al., J. Vasc. Interv. Radiol., 19:252-259 (2008)). HIF-1α staining was quantified to assess whether S treated vessels had decreased expression of HIF-1α when compared to controls. Brown staining nuclei were positive for HIF-1α (FIG. 11A, upper panel). By day 7, there was significant reduction in the average density of HIF-1α staining in the S treated vessels when compared to C vessels (average reduction: 71%, P<0.0001, FIG. 11B). By day 21, the average density of HIF-1α staining remained significantly lower in the S treated vessels when compared to C vessels (average reduction: 69%, P<0.0001).

CorMatrix™ Wrapped Outflow Vein has Reduced CD68 Staining when Compared to Control Vessels Other studies demonstrated increased CD68 expression (a marker for macrophages) in animal models of hemodialysis graft failure and in clinical specimens from patients with hemodialysis vascular access failure (Misra et al., J. Vasc. Interv. Radiol., 21:1255-1261 (2010); and Misra et al., J. Vasc. Interv. Radiol., 19:252-259 (2008)). CD68 staining was quantified to assess whether the S treated vessels had an effect on the expression of macrophage at the outflow vein of AVF. Cells staining brown in the cytoplasm were positive for CD68 (FIG. 11A, lower panel). By day 7, there was significant reduction in the average density of CD68 staining in the S treated vessels when compared to C vessels (average reduction: 71%, P<0.0001, FIG. 11C) that remained significantly decreased by day 21 (average reduction: 63%, P<0.05). Overall, these results indicate that S treated vessels when compared to C vessels have decreased CD68 (+) staining.

These results demonstrate that extracellular matrix scaffolds (e.g., CorMatrix™) can be used to wrap vessels in a manner that reduces VNH. This is accompanied by a significant increase in TUNEL staining and a decrease in proliferation. In addition, there is a significant decrease in the FSP-1, CD68, and α-SMA staining accompanied with a decrease in average HIF-1α staining.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing venous neointimal hyperplasia formation of an arteriovenous fistula or graft in a mammal, wherein said method comprises applying small-intestine submucosa to an adventitia of a vein of said arteriovenous fistula or graft under conditions wherein venous neointimal hyperplasia formation of said arteriovenous fistula or graft is reduced.

2. The method of claim 1, wherein said mammal is a human.

3. The method of claim 1, wherein said small-intestine submucosa is porcine small-intestine submucosa.

4. The method of claim 1, wherein said small-intestine submucosa is applied by wrapping said small-intestine submucosa around said adventitia of said vein.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Mus musculus

<400> SEQUENCE: 1
ggagagctac aagaggatca c                                             21

<210> SEQ ID NO 2
<211> LENGTH: 22
<212> TYPE: DNA
<213> ORGANISM: Mus musculus

<400> SEQUENCE: 2
tgatctcatt tggttccgat cc                                            22

<210> SEQ ID NO 3
<211> LENGTH: 20
<212> TYPE: DNA
<213> ORGANISM: Mus musculus

```
<400> SEQUENCE: 3
ttgctcatga catcgaccag                                              20

<210> SEQ ID NO 4
<211> LENGTH: 20
<212> TYPE: DNA
<213> ORGANISM: Mus musculus

<400> SEQUENCE: 4
acatcaaagg tctcacaggc                                              20

<210> SEQ ID NO 5
<211> LENGTH: 21
<212> TYPE: DNA
<213> ORGANISM: Mus musculus

<400> SEQUENCE: 5
cccagatgta ccaggattct c                                            21

<210> SEQ ID NO 6
<211> LENGTH: 22
<212> TYPE: DNA
<213> ORGANISM: Mus musculus

<400> SEQUENCE: 6
agcttgtcta cttcagtcat gg                                           22

<210> SEQ ID NO 7
<211> LENGTH: 21
<212> TYPE: DNA
<213> ORGANISM: Mus musculus

<400> SEQUENCE: 7
gttccgacca taaacgatgc c                                            21

<210> SEQ ID NO 8
<211> LENGTH: 21
<212> TYPE: DNA
<213> ORGANISM: Mus musculus

<400> SEQUENCE: 8
tggtggtgcc cttccgtcaa t                                            21
```